US007572443B2

(12) United States Patent
Debs (10) Patent No.: US 7,572,443 B2
(45) Date of Patent: Aug. 11, 2009

(54) ANTI-PECAM THERAPY FOR METASTASIS SUPPRESSION

(75) Inventor: Robert Debs, Mill Valley, CA (US)

(73) Assignee: California Pacific Medical Center, San Francisco, CA (US)

( * ) Notice: Subject to any disclaimer, the term of this patent is extended or adjusted under 35 U.S.C. 154(b) by 0 days.

(21) Appl. No.: 10/988,423

(22) Filed: Nov. 12, 2004

(65) Prior Publication Data

US 2005/0186213 A1 Aug. 25, 2005

Related U.S. Application Data

(60) Provisional application No. 60/519,986, filed on Nov. 13, 2003.

(51) Int. Cl.
*A61K 39/00* (2006.01)
*A61K 39/395* (2006.01)
(52) U.S. Cl. .............. 424/130.1; 424/277.1; 424/141.1
(58) Field of Classification Search ....................... None
See application file for complete search history.

(56) References Cited

U.S. PATENT DOCUMENTS

| | | | |
|---|---|---|---|
| 4,683,202 | A | 7/1987 | Mullis |
| 4,816,567 | A | 3/1989 | Cabilly et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,968,511 | A | 10/1999 | Akita et al. |
| 6,133,426 | A | 10/2000 | Gonzalez et al. |
| 6,627,196 | B1 | 9/2003 | Baughman et al. |
| 6,639,055 | B1 | 10/2003 | Carter et al. |

FOREIGN PATENT DOCUMENTS

| | | |
|---|---|---|
| EP | 0 404 097 B1 | 12/1990 |
| IE | 902254 | 6/1990 |
| WO | WO 93/11161 A1 | 6/1993 |
| WO | WO 01/55178 A2 | 8/2001 |
| WO | WO 02/085405 A2 | 10/2002 |
| WO | WO 03/055516 A1 | 7/2003 |

OTHER PUBLICATIONS

Jain R. K. Scientific American, 271(1): 58-65, Jul. 1994.*
Dillman R. O., Annals of Internal Medicine, 111:592-603, 1989.*
Weiner L. M. Seminars in Oncology, 26 (4 Suppl 12): 41-50, Aug. 1999.*
Zhou et al., Angiogenesis, vol. 3, p. 181-188, 1999.*
Weidner et al., Am J Pathol, vol. 143, p. 401-9, 1993.*
Yang et al., N Engl J Med. vol. 349, p. 427-434, 2003.*
Gerber et al., PNAS, vol. 104, p. 3478-3483, 2007.*
Passaniti et al., J Biol Chem. vol. 263 p. 7591-7603, 1998. Abstract.*
Lundy et al.,., J. Surg. Oncol. vol. 31 p. 260-7. 1986. Abstract.*
Wong et al.,., Amer. J. of Path. vol. 161, p. 749-53. 2002.*
Baker, et al., "Suppression of human colorectal carcinoma cell growth by wild-type p53." *Science* 249:912-915 (1990).
Barbas, et al., "Semisynthetic combinatorial antibody libraries: a chemical solution to the diversity problem." *Proc. Nat'l Acad. Sci. USA* 89:4457-4461 (1992).
Boerner, et al., "Production of antigen-specific human monoclonal antibodies from in vitro-primed human splenocytes." *J. Immunol.* 147:86-95 (1991).
Breitling, et al., "A surface expression vector for antibody screening." *Gene* 104:147-153 (1991).
Burton, et al., "A large array of human monoclonal antibodies to type 1 human immunodeficiency virus from combinatorial libraries of asymptomatic seropositive individuals." *Proc. Nat'l Acad. Sci USA* 88:10134-10137 (1991).
Cao, et al., "Involvement of human PECAM-1 in angiogenesis and in vitro endothelial cell migration." *Am. J. Physiol. Cell Physiol.* 282:C1181-C1190 (2002).
Caton and Koprowski, "Influenza virus hemagglutinin-specific antibodies isolated from a combinatorial expression library are closely related to the immune response of the donor." *Proc. Nat'l Acad. Sci. USA* 87:6450-6454 (1990).
Chang, et al., "Expression of antibody Fab domains on bacteriophage surfaces. Potential use for antibody selection." *J. Immunol.* 147:3610-3614 (1991).
Chothia and Lesk, "Canonical structures for the hypervariable regions of immunoglobulins." *J. Mol. Biol.* 196:901-917 (1987).
Clackson, et al., "Making antibody fragments using phage display libraries." *Nature* 352:624-628 (1991).
Cole, et al., "The EBV-hybridoma technique and its application to human lung cancer" in *Monoclonal Antibodies and Cancer Therapy*, Alan R. Liss, p. 77-96 (1985).
Desprez, et al., "A novel pathway for mammary epithelial cell invasion by helix-loop-helix protein Id-1." *Mol. Cell Biol.* 18:4577-4588 (1998).
Duncan, et al., "Genetic evidence for functional redundancy of platelet/endothelial cell adhesion molecule-1 (PECAM-1): CD31-deficient mice reveal PECAM-1-dependent and PECAM-1-independent functions." *J. Immunol.* 162:3022-3030 (1999).
Eckert and Kunkel, "DNA polymerase fidelity and the polymerase chain reaction". *PCR Methods and Applications* 1:17-24 (1991).
Ellisen and Haber, "Hereditary breast cancer." *Annu Rev Med.* 49:425-36 (1998).
Evan and Littlewood, "A matter of life and cell death." *Science* 28:1317-22 (1998).
Fishwild, et al., "High-avidity human IgG kappa monoclonal antibodies from a novel strain of minilocus transgenic mice." *Nature Biotechnol.* 14:845-51 (1996).

(Continued)

*Primary Examiner*—Larry R. Helms
*Assistant Examiner*—Lei Yao
(74) *Attorney, Agent, or Firm*—Karen E. Flick (57) ABSTRACT

The invention provides novel compositions, methods, kits, and uses thereof relating to antimetastatic agents useful for treating neoplastic diseases.

11 Claims, 5 Drawing Sheets

OTHER PUBLICATIONS

Foulds, "The natural history of cancer." *J Chronic Dis.* 8:2-37 (1958).

Hawkins and Winter, "Cell selection strategies for making antibodies from variable gene libraries: trapping the memory pool." *Eur. J. Immunol.* 22:867-870 (1992).

Holliger, et al., "Diabodies: small bivalent and bispecific antibody fragments." *Proc. Nat'l Acad. Sci. USA* 90:6444-6448 (1993).

Hoogenboom and Winter, "By-passing immunisation. Human antibodies from synthetic repertoires of germline $V_H$ gene segments rearranged in vitro." *J. Mol. Biol.* 227:381-388 (1992).

Hoogenboom, et al., "Multi-subunit proteins on the surface of filamentous phage: methodologies for displaying antibody (Fab) heavy and light chains." *Nucleic Acids Res.* 19:4133-4137 (1991).

Huse, et al., "Generation of a large combinatorial library of the immunoglobulin repertoire in phage lambda." *Science* 246:1275-1281 (1989).

Jones, et al., "Replacing the complementarity-determining regions in a human antibody with those from a mouse." *Nature* 321:522-525 (1986).

Kabat, et al., *Sequences of Proteins of Immunological Interest*, NIH Publ No. 91-3242, vol. I, pp. 647-669 (1991).

Kang, et al., "Linkage of recognition and replication functions by assembling combinatorial antibody Fab libraries along phage surfaces." *Proc. Nat'l Acad. Sci. USA* 88: 4363-4366 (1991).

Kerr, et al., "Apoptosis: a basic biological phenomenon with wide-ranging implications in tissue kinetics." *Br. J. Cancer* 26:239-257 (1972).

Kohler and Milstein, "Continuous cultures of fused cells secreting antibody of predefined specificity." *Nature* 256:495-497 (1975).

Lee, et al., "Human retinoblastoma susceptibility gene: cloning, identification, and sequence." *Science* 235:1394-1399 (1987).

Lerner, et al., "Antibodies without immunization." *Science* 258:1313-1314 (1992).

Lonberg, et al., "Antigen-specific human antibodies from mice comprising four distinct genetic modifications." *Nature* 368:856-859 (1994).

Lonberg and Huszar, "Human antibodies from transgenic mice." *Intem. Rev. Immunol.* 13:65-93 (1995).

Lowman, et al., "Selecting high-affinity binding proteins by monovalent phage display ." *Biochemistry* 30:10832-10838 (1991).

Marks, et al., "By-passing immunization: building high affinity human antobodies by chain shuffling." *Biotechnol.* 10:779-783 (1992).

Marks, et al., "Molecular evolution of proteins on filamentous phage. Mimicking the strategy of the immune system." *J. Biol. Chem.* 267:16007-16010 (1992).

Marks, et al., "By-passing immunization. Human antibodies from V-gene libraries displayed on phage." *J. Mol. Biol.* 222:581-597 (1991).

Mattila, et al., "Fidelity of DNA synthesis by the *Thermococcus litoralis* DNA polymerase—an extremely heat stable enzyme with proofreading activity." *Nucl. Acids Res.* 19:4967-4973 (1991).

Molecular Probes Product Information, "Labeled Donkey Anti-Goat IgG Antibodies." MP11055, Sep. 20, 1-2 (2001).

Morrison, "Success in specification." *Nature* 368:812-813 (1994).

Morrison, et al., "Chimeric human antibody molecules: Mouse antigen-binding domains with human constant region domains." *Proc. Nat'l Acad. Sci. USA* 81:6851-6955 (1984).

Mullinax, et al., "Identification of human antibody fragment clones specific for tetanus toxoid in a bacteriophage γ immunoexpression library." *Proc. Nat'l Acad. Sci. USA* 87:8095-8099 (1990).

Nakada, et al., "Antibodies against the first Ig-like domain of human platelet endothelial cell adhesion molecule-1 (PECAM-1) that Inhibit PECAM-1-dependent homophilic adhesion block in vivo neutrophil recruitment." *J. Immunol.* 164:452-462 (2000).

Needleman and Wunsch, "A general method applicable to the search for similarities in the amino acid sequence of two proteins." *J. Mol. Biol.* 48:443-453(1970).

Neuberger, "Generating high-avidity human Mabs in mice." *Nature Biotechnol.* 14:826 (1996).

Pearson and Lipman, "Improved tools for biological sequence comparison." *Proc. Nat'l Acad. Sci. USA* 85:2444-2448 (1988).

Persson, et al., "Generation of diverse high-affinity human monoclonal antibodies by repertoire cloning." *Proc. Nat'l Acad. Sci. USA* 88:2432-2436 (1991).

Pluckthun, "Antibodies from *Escherichia coli*" in *The Pharmacology of Monoclonal Antibodies*, vol. 113, Rosenberg and Moore, eds. Springer-Verlag, New York, pp. 269-315 (1994).

Presta, "Antibody engineering." *Curr. Opin. Struct. Biol.* 2:593-596 (1992).

Riechmann, et al., "Reshaping human antibodies for therapy." *Nature* 332:323-327 (1988).

Smith and Waterman, "Comparison of Biosequences." *Adv. Appl. Math.* 2:482-489 (1981).

van Diest, et al., "Proliferation markers in tumors: interpretation and clinical value." *J. Clin. Pathol.* 51:716-724 (1998).

Verhoeyen, et al., "Reshaping human antibodies: grafting an antilysozyme activity." *Science* 239:1534-1536 (1988).

Weinberg, "The molecular basis of retinoblastomas" *Genetic Analysis of Tumour Suppression*, Ciba Found Symp. 142:99-111 (1989).

Young and Davis, "Efficient isolation of genes by using antibody probes." *Proc. Nat'l Acad. Sci. USA* 80:1194-1198 (1983).

Zapata, et al., "Engineering linear F(ab')2 fragments for efficient production in *Escherichia coli* and enhanced antiproliferative activity." *Protein Eng.* 8:1057-1062 (1995).

Zhou, et al., "Antibody against murine PECAM-1 inhibits tumor angiogenesis in mice." *Angiogenesis* 3:181-188 (1999).

Tang, et al., "Identification of PECAM-1 in solid tumor cells and its potential involvement in tumor cell adhesion to endothelium." *J. Biol. Chem.* 268:22883-22894 (1993).

Kashani-Sabet, et al., "Identification of gene function and functional pathways by systemic plasmid-based ribozyme targeting in adult mice." *Proc. Nat'l Acad. Sci. USA* 99:3878-3883 (2002).

Delisser et al., "Short Communication, Involvement of Endothelial PECAM-1/CD31 in Angiogenesis", *American Journal of Pathology* 151(3):671-677 (1997).

Sacchi et al., "Treatment With Monoclonal Antibody to a Lewis Lung Carcinoma-Associated Antigen: Different Effects on Primary Tumor and its Metastases", *Cancer Treatment Reports* 69(9):985-991 (1985).

Scherpereel, et al., "Platelet-Endothelial Cell Adhesion Molecule-1-Directed Immunotargeting to Cardiopulmonary Vasculature", *Journal of Pharmacology and Experimental Therapeutics* 300(3):777-786 (2002).

Thai et al., "Physical proximity and functional interplay of PECAM-1 with the Fc receptor FcγRlIa on the platelet plasma membrane", *Hemostasis, Thrombosis and Vascular Biology* 102(10):3637-3645 (2003).

* cited by examiner

ANTI-PECAM THERAPY FOR METASTASIS SUPPRESSION

CROSS-REFERENCE

This application claims priority to N.S. Provisional Patent Application No. 60/519,986 filed 13 Nov. 2003, which is incorporated by reference herein.

FIELD OF THE INVENTION

The invention relates to the identification of a method and related compositions for inhibiting the metastatic capability of neoplastic cells in a patient. The methods and compositions comprise a PECAM-binding agent, such as an antibody, and methods of treating or preventing disease using a PECAM-binding agent to modulating invasiveness and metastatic potential of neoplastic cells.

BACKGROUND OF THE INVENTION

Oncogenesis was described by Foulds (1958) as a multi-step biological process, which is presently known to occur by the accumulation of genetic damage. On a molecular level, the multistep process of tumorigenesis involves the disruption of both positive and negative regulatory effectors (Weinberg, 1989). The molecular basis for human colon carcinomas has been postulated, by Vogelstein and coworkers (1990), to involve a number of oncogenes, tumor suppressor genes and repair genes. Similarly, defects leading to the development of retinoblastoma have been linked to another tumor suppressor gene (Lee et al., 1987). Still other oncogenes and tumor suppressors have been identified in a variety of other malignancies. Unfortunately, there remains an inadequate number of treatable cancers, and the effects of cancer are catastrophic—over half a million deaths per year in the United States alone.

Cancer is fundamentally a genetic disease in which damage to cellular DNA leads to disruption of the normal mechanisms that control cellular proliferation. Two of the mechanisms of action by which tumor suppressors maintain genomic integrity is by cell arrest, thereby allowing for repair of damaged DNA, or removal of the damaged DNA by apoptosis (Ellisen and Haber, 1998; Evan and Littlewood, 1998). Apoptosis, otherwise called "programmed cell death," is a carefully regulated network of biochemical events which act as a cellular suicide program aimed at removing irreversibly damaged cells. Apoptosis can be triggered in a number of ways including binding of tumor necrosis factor, DNA damage, withdrawal of growth factors, and antibody cross-linking of Fas receptors. Although several genes have been identified that play a role in the apoptotic process, the pathways leading to apoptosis have not been fully elucidated. Many investigators have attempted to identify novel apoptosis-promoting genes with the objective that such genes would afford a means to induce apoptosis selectively in neoplastic cells to treat cancer in a patient.

An alternative approach to treating cancer involves the suppression of angiogenesis with agent such as Endostatin™ or anti-VEGF antibodies. In this approach, the objective is to prevent further vascularization of the primary tumor and potentially to constrain the size of metastatic lesions to that which can support neoplastic cell survival without substantial vascular growth.

Platelet endothelial cell adhesion molecule (PECAM-1; CD31) is a protein found on endothelial cells and neutrophils and has been shown to be involved in the migration of leukocytes across the endothelium. The modulation of the activity of PECAM-1 for the treatment of cardiovascular conditions such as thrombosis, vascular occlusion stroke and for the treatment of or for reducing the occurrence of haemostasis disorders is disclosed in WO03055516A1. PECAM-1 has also been implicated in the inflammatory process and anti-PECAM-1 monoclonal antibody has been reported to block in vivo neutrophil recruitment (Nakada et al. (2000) *J. Immunol.* 164: 452-462). PECAM-1 knockout mice have been reported and appear to have normal leukocyte migration, platelet aggregaton, and vascular development, which implies that there are redundant adhesion molecules which can compensate for a loss of PECAM-1 (Duncan et al. (1999) *J. Immunol.* 162: 3022-3030). Monoclonal antibodies to PECAM-1 have been reported to block murine endothelial tube formation and related indicators of vascularization in a tumor transplantation model (Zhou et al. (1999) *Angiogenesis* 3: 181-188 and in a human skin transplantation model (Cao et al. (2002) *Am. J. Physiol. Cell Physiol.* 282: C1181-C1190). However, the role of PECAM-1 in tumor angiogenesis, if any, remains undefined.

Despite substantial efforts to inhibit cancer and the metastasis of tumors with anti-angiogenic strategies, to date there are no approved and marketed drugs for treating cancer solely by the inhibition of angiogenesis. Indeed the specific roles of various adhesion molecules, including PECAM-1, in the processes of neoplasia and metastasis are unknown.

There exists a need in the art for a method and related compositions for inhibiting the metastatic potential of cancer cells in patients. The present invention fulfills this need and provides related aspects desired by practitioners in the field.

The references discussed herein are provided solely for their disclosure prior to the filing date of the present application. Nothing herein is to be construed as an admission that the inventors are not entitled to antedate such disclosure by virtue of prior invention. All patent and literature publications referenced herein are incorporated by reference for all purposes as if the entire content of the disclosures were mechanically or electronically reproduced herein.

SUMMARY OF THE INVENTION

The present invention relates to the unexpected discovery that systemic administration of an antibody that binds to PECAM-1 supresses the metastatic spread of a wide variety of different tumor types which are typically fatal in humans, and this effect is achieved independent from any inhibition of angiogenesis, if any. This unexpected discovery provides a basis for the generation of novel anticancer treatments and medicaments, wherein provision of a systemic dosage of anti-PECAM antibody or a proxy that provides the same functional result is administered to a patient to inhibit or reduce the invasiveness and/or metastatic potential of neoplastic cells in the patient.

The present invention provides methods for repressing or preventing neoplastic transformation in a cell, the method comprising administering an anti-PECAM antibody systemically in an amount effective to inhibit the transformed phenotype and reduce the detectable invasiveness and/or metastatic potential of the cell. In an embodiment, the anti-PECAM antibody can bind to a PECAM located on a non-neoplastic somatic cell or it can bind to PECAM or a cross-reactive macromolecule present on a neoplastic cell.

An anti-PECAM binding species may be contacted with or introduced to a patient who has been diagnosed with a neoplasm through any of a variety of manners known to those of skill, however it is often preferred to deliver the anti-PECAM binding agent systemically. With regard to the invention, an anti-PECAM binding species can comprise an antibody, such as a humanized or human-sequence monoclonal antibody, and antibody fragment that comprises F(ab)2, F(ab')2, F9ab, F(ab), Dab, Fv, scFv, Fc or a minimal recognition unit of an antibody that has the property of binding to human PECAM-1 with an affinity of at least about $1 \times 10^8$ M. Alternative binding species can also include, but are not limited to, proteinaceous binding multimers according to U.S. 20030157561A1 high-affinity peptides, and equivalents. In some embodiments, the anti-PECAM binding species is covalently linked to poly(ethylene)glycol (PEG), such as a 30K linear PEG, or 40K, 60K, or larger branched PEG—or larger linear or branched PEG moieties, either via single attachment or via multiple attachments.

In some embodiments of the present invention, the inventor's discovery that anti-PECAM binding species administered systemically is able to inhibit metastasis will be used in combination with other anti-transformation/anti-cancer therapies. These other therapies may be known at the time of this application, or may become apparent after the date of this application. For example, a humanized or human sequence anti-PECAM antibody may be used in combination with other therapeutic polypeptides, polynucleotides encoding other therapeutic polypeptides, or chemotherapeutic agents. In one representative embodiment, the chemotherapeutic agent is taxol. The anti-PECAM binding species also may be used in conjunction with radiotherapy. The type of ionizing radiation constituting the radiotherapy may be selected from the group comprising x-rays, gamma-rays, and microwaves. In certain embodiments, the ionizing radiation may be delivered by external beam irradiation or by administration of a radionuclide. The anti-PECAM binding species also may be used with gene therapy regimes.

The present invention also provides treatment methods for many human cancers. The treatment method comprises treating a patient having a diagnosed neoplasm, typically a carcinoma or sarcoma or other solid tumor type, with a systemic dosage of anti-PECAM binding species preferably delivered via subcutaneous or intravenous administration, or intrathecally into the brain to inhibit brain metastases. Preferred variations of the method include treating a patient having a diagnosed breast carcinoma, lung carcinoma, or colon carcinoma by administering an effective dose of an anti-PECAM binding species, such as a humanized or human-sequence anti-PECAM monoclonal antibody via a systemic route such as subcutaneous or intravenous.

In certain other aspects of the present invention there are provided therapeutic kits comprising in suitable container, a pharmaceutical formulation of an anti-PECAM binding species. Such a kit may further comprise a pharmaceutical formulation of a therapeutic polypeptide, polynucleotide encoding a therapeutic polypeptide, or chemotherapeutic agent. Such kits may comprise radiosensitizing agents, instructions for administration of an anti-PECAM binding species to a human patient diagnosed with a neoplasm—particularly a lung, colon, or breast neoplasm or in a variation a melanoma—via systemic delivery. In a preferred variation, the kit comprises a humanized or human sequence anti-PECAM monoclonal antibody which is PEGylated.

The invention also provides antibodies which bind to human PECAM-1 with an affinity of about at least $1 \times 10^7$ M$^{-1}$ and which lack specific high affinity binding for a other PECAM-related polypeptides. Such antibodies may be used therapeutically by systemic, intracranial, or targeted delivery to neoplastic cells (e.g., by cationization or by liposome or immunoliposome delivery).

The invention also provides therapeutic agents which inhibit neoplasia, invasiveness and/or metastasis by modulating PECAM-1 function and which do not inhibit angiogenesis; such agents can be used as pharmaceuticals.

The invention provides a method for treating patients who have a diagnosed solid tumor and for whom angiogenesis inhibition would be detrimental; such as patients having recently suffered a myocardial infarction, congestive heart failure, stroke, atherosclerosis of the coronary vessels or cerebrovasculature, or who have a significant wound healing process resulting from injury or major surgery and which benefit from angiogenesis to aid healing or restore circulation.

In a variation of the invention, an immunogenic dose of a denatured human PECAM-1 or a non-human PCAM-1 such as primate, mouse, rat, dog, or pig PECAM-1 protein or a portion thereof is administered to a human patient diagnosed with a neoplasm, typically in combination with an adjuvant and/or a covalently-attached or non-attached immunostimulatory polynucleotide such as those disclosed by Dynavax or Coley Pharmaceuticals. In this way, the human patient is able to make an immune response, including an antibody response, which will crossreact with their own PECAM-1 protein which they are otherwise tolerized to.

A further understanding of the nature and advantages of the invention will become apparent by reference to the remaining portions of the specification and drawings.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The following patent documents are incorporated herein by reference:

U.S. Pat. No. 5,968,511; WO0155178; U.S. Pat. Nos. 6,639,055; 6,133,426; WO03055516; WO02085405; and U.S. Pat. No. 6,627,196—including methods and materials described therein.

Definitions

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 2, or may comprise a complete cDNA or gene sequence. Generally, a reference sequence is at least 20 nucleotides in length, frequently at least 25 nucleotides in length, and often at least 50 nucleotides in length. Since two olynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (*U.S.A.*) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion, but where the remaining amino acid sequence is identical to the corresponding positions in the sequence deduced from a full-length cDNA. Fragments typically are at least 14 amino acids long, preferably at least 20 amino acids long, usually at least 50 amino acids long or longer, up to the length of a full-length naturally-occurring polypeptide.

The term "agent" is used herein to denote a chemical compound, a mixture of chemical compounds, an array of spatially localized compounds (e.g., a VLSIPS peptide array, polynucleotide array, and/or combinatorial small molecule array), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues. Agents are evaluated for potential activity as antineoplastics, anti-inflammatories, or apoptosis modulators by inclusion in screening assays described hereinbelow. Agents are evaluated for potential activity as specific protein interaction inhibitors (i.e., an agent which selectively inhibits a binding interaction between two predetermined polypeptides but which does not substantially interfere with cell viability) by inclusion in screening assays described hereinbelow.

The term "protein interaction inhibitor" is used herein to refer to an agent which is identified by one or more screening method(s) of the invention as an agent which selectively inhibits protein-protein binding between a first interacting polypeptide and a second interacting polypeptide. Some protein interaction inhibitors may have therapeutic potential as drugs for human use and/or may serve as commercial reagents for laboratory research or bioprocess control. Protein interaction inhibitors which are candidate drugs are then tested further for activity in assays which are routinely used to predict suitability for use as human and veterinary drugs, including in vivo administration to non-human animals and often including administration to human in approved clinical trials.

The term "antineoplastic agent" is used herein to refer to agents that have the functional property of inhibiting a development or progression of a neoplasm in a human, particularly a metastasis-prone solid tumor type.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein "normal blood" or "normal human blood" refers to blood from a healthy human individual who does not have an active neoplastic disease or other disorder of lymphocytic proliferation, or an identified predisposition for developing a neoplastic disease. Similarly, "normal cells", "normal cellular sample", "normal tissue", and "normal lymph node" refers to the respective sample obtained from a healthy human individual who does not have an active neoplastic disease or other lymphoproliferative disorder.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45° C. and 0.001-10 mM divalent cation (e.g., Mg$^{++}$, Ca$^{++}$); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or nonionic detergents and/or membrane fractions and/or anti-foam agents and/or scintillants.

As used herein, the terms "interacting polypeptide segment" and "interacting polypeptide sequence" refer to a portion of a hybrid protein which can form a specific binding interaction with a portion of a second hybrid protein under suitable binding conditions. Generally, a portion of the first hybrid protein preferentially binds to a portion of the second hybrid protein forming a heterodimer or higher order heteromultimer comprising the first and second hybrid proteins; the binding portions of each hybrid protein are termed interacting polypeptide segments. Generally, interacting polypeptides can form heterodimers with a dissociation constant ($K_D$) of at least about $1\times10^3$ M$^{-1}$, usually at least $1\times10^4$ M$^{-1}$, typically at least $1\times10^5$ M$^{-1}$, preferably at least $1\times10^6$ M$^{-1}$ to $1\times10^7$ M$^{-1}$ or more, under suitable physiological conditions.

As used herein, the term "multimer" comprises dimer and higher order complexes (trimer, tetramer, pentamer, hexamer, heptamer, octamer, etc.). "Homomultimer" refers to complexes comprised of the same subunit species. "Heteromultimer" refers to complexes comprised of more than one subunit species.

The term "recombinant" used herein refers to PECAM-1 produced by recombinant DNA techniques wherein the gene coding for protein is cloned by known recombinant DNA technology. For example, the human gene for PECAM-1 may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, *Aspergillus* and insect cells.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas. The term "antibody" is used in the broadest sense and specifically covers, without limitation, intact monoclonal antibodies, polyclonal antibodies, multispecific antibodies (e.g., bispecific antibodies) formed from at least two intact antibodies, and antibody fragments so long as they exhibit the desired biological activity.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR) regions. The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., NIH Publ. No. 91-3242, Vol. I, pages 647-669 (1991)). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institute of Health, Bethesda, Md. [1991]) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Clothia and Lesk, J. Mol. Biol., 196:901-917 [1987]). "Framework" or "FR" residues are those variable domain residues other than the hypervariable region residues as herein defined.

"Antibody fragments" comprise a portion of an intact antibody, preferably the antigen binding or variable region of the intact antibody. Examples of antibody fragments include Fab, Fab', F(ab').sub.2, and Fv fragments; diabodies; linear antibodies (Zapata et al., Protein Eng., 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab').sub.2 fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the V.sub.H-V.sub.L dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (.kappa.) and lambda (.lambda.), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are known.

The term "monoclonal antibody" as used herein refers to an antibody obtained from a population of substantially homogeneous antibodies, i e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 [1975], or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 [1991] and Marks et al., J. Mol. Biol., 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 [1984]).

"Humanized" forms of non-human (e.g., murine) antibodies are chimeric immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fe), typically that of a human immunoglobulin. For further details, see, Jones et al., Nature, 321:522-525 (1986); Reichmann et al., Nature, 332:323-329 [1988]; and Presta, Curr. Op. Struct. Biol., 2:593-596 (1992). The humanized antibody include PRIMATIZED.TM. antibody wherein the antigen-binding region of the antibody is derived from an antibody produced by immunizing macaque monkeys with the antigen of interest.

"Single-chain Fv" or "sFv" antibody fragments comprise the V.sub.H and V.sub.L domains of antibody, wherein these domains are present in a single polypeptide chain. Preferably, the Fv polypeptide further comprises a polypeptide linker between the V.sub.H and V.sub.L domains which enables the sFv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (V.sub.H) connected to a light-chain variable domain (V.sub.L) in the same polypeptide chain (V.sub.H-V.sub.L). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

DETAILED DESCRIPTION OF THE INVENTION

The nomenclature used hereafter and the laboratory procedures in cell culture, molecular genetics, and nucleic acid chemistry and hybridization described below may involve well known and commonly employed procedures in the art. Standard techniques are used for recombinant nucleic acid methods, polynucleotide synthesis, and microbial culture and transformation (e.g., electroporation, lipofection). The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document.

Oligonucleotides can be synthesized on an Applied Bio Systems oligonucleotide synthesizer according to specifications provided by the manufacturer.

Methods for PCR amplification are described in the art (PCR Technology: Principles and Applications for DNA Amplification ed. HA Erlich, Freeman Press, New York, N.Y. (1992); PCR Protocols: A Guide to Methods and Applications, eds. Innis, Gelfland, Snisky, and White, Academic Press, San Diego, Calif. (1990); Mattila et al. (1991) Nucleic Acids Res. 19: 4967; Eckert, K. A. and Kunkel, T. A. (1991) PCR Methods and Applications 1: 17; PCR, eds. McPherson, Quirkes, and Taylor, IRL Press, Oxford; and U.S. Pat. No. 4,683,202, which are incorporated herein by reference).

Production and Applications of α-PECAM Antibodies

Native human PECAM-1 proteins, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see Antibodies: A Laboratory Manual, (1988) E. Harlow and D. Lane, Cold Spring Harbor Laboratory, Cold Spring Harbor, N.Y., which is incorporated herein by reference.

For example but not for limitation, a recombinantly produced fragment of PECAM-1 can be injected into a mouse along with an adjuvant following immunization protocols known to those of skill in the art so as to generate an immune response. Typically, approximately at least 1-50 μg of a PECAM-1 fragment or analog is used for the initial immunization, depending upon the length of the polypeptide. Alternatively or in combination with a recombinantly produced PECAM-1 polypeptide, a chemically synthesized peptide having a PECAM-1 sequence may be used as an immunogen to raise antibodies which bind a PECAM-1 protein, such as the native PECAM-1 polypeptide having the sequence shown essentially in FIG. 1(a), a native human PECAM-1 polypeptide, a polypeptide comprising a PECAM-1 epitope, or a PECAM-1 fusion protein. Immunoglobulins which bind the recombinant fragment with a binding affinity of at least $1 \times 10^7$ $M^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly-produced PECAM-1 polypeptide (or chemically synthesized PECAM-1 polypeptide) with an affinity of at least $1 \times 10^6 \, M^{-1}$. Animals other than mice and rats may be used to raise antibodies; for example, goats, rabbits, sheep, and chickens may also be employed to raise antibodies reactive with a PECAM-1 protein. Transgenic mice having the capacity to produce substantially human antibodies also may be immunized and used for a source of α-PECAM-1 antiserum and/or for making monoclonal-secreting hybridomas.

Bacteriophage antibody display libraries may also be screened for binding to a PECAM-1 polypeptide, such as a full-length PECAM-1 protein, a PECAM-1 fragment, or a fusion protein comprising a PECAM-1 polypeptide sequence comprising a PECAM-1 epitope (generally at least 3-5 contiguous amino acids). Generally such PECAM-1 peptides and the fusion protein portions consisting of PECAM-1 sequences for screening antibody libraries comprise about at least 3 to 5 contiguous amino acids of PECAM-1, frequently at least 7 contiguous amino acids of PECAM-1, usually comprise at least 10 contiguous amino acids of PECAM-1, and most usually comprise a PECAM-1 sequence of at least 14 contiguous amino acids.

Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (U.S.A.)* 88: 2432). Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl. Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science* 258: 1313, incorporated herein by reference). Typically, a bacteriophage antibody display library is screened with a PECAM-1 polypeptide that is immobilized (e.g., by covalent linkage to a chromatography resin to enrich for reactive phage by affinity chromatography) and/or labeled (e.g., to screen plaque or colony lifts).

PECAM-1 polypeptides which are useful as immunogens, for diagnostic detection of α-PECAM-1 antibodies in a sample, for diagnostic detection and quantitation of PECAM-1 protein in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other proteins of humans, mice, or other contaminants.

For some applications of these antibodies, such as identifying immunocrossreactive proteins, the desired antiserum or monoclonal antibody(ies) is/are not monospecific. In these instances, it may be preferable to use a synthetic or recombinant fragment of PECAM-1 as an antigen rather than using the entire native protein. Production of recombinant or synthetic fragments having such defined amino- and carboxytermini is provided by the PECAM-1.

If an antiserum is raised to a PECAM-1 fusion polypeptide, such as a fusion protein comprising a PECAM-1 immunogenic epitope fused to β-galactosidase or glutathione S-transferase, the antiserum is preferably preadsorbed with the non-PECAM-1 fusion partner (e.g, β-galactosidase or glutathione S-transferase) to deplete the antiserum of antibodies that react (i.e., specifically bind to) the non-PECAM-1 portion of the fusion protein that serves as the immunogen. Monoclonal or polyclonal antibodies which bind to the human and/or murine PECAM-1 protein can be used to detect the presence of human or murine PECAM-1 polypeptides in a sample, such as a Western blot of denatured protein (e.g., a nitrocellulose blot of an SDS-PAGE) obtained from a lymphocyte sample of a patient. Preferably quantitative detection is performed, such as by denistometric scanning and signal integration of a Western blot. The monoclonal or polyclonal antibodies will bind to the denatured PECAM-1 epitopes and may be identified visually or by other optical means with a labeled second antibody or labeled *Staphylococcus aureus* protein A by methods known in the art.

One use of such antibodies is to screen cDNA expression libraries, preferably containing cDNA derived from human or murine mRNA from various tissues, for identifying clones containing cDNA inserts which encode structurally-related, immunocrossreactive proteins, that are candidate novel PECAM-1 binding factors or PECAM-1-related proteins. Such screening of cDNA expression libraries is well known in the art, and is further described in Young et al., *Proc. Natl. Acad. Sci. U.S.A.* 80:1194-1198 (1983), which is incorporated herein by reference) as well as other published sources. Another use of such antibodies is to identify and/or purify immunocrossreactive proteins that are structurally or evolutionarily related to the native PECAM-1 protein or to the corresponding PECAM-1 fragment (e.g., functional domain; PECAM-1-interacting protein binding domain) used to generate the antibody. The anti-PECAM-1 antibodies of the invention can be used to measure levels of PECAM-1 protein in a cell or cell population, for example in a cell explant (e.g., lymphocyte sample) obtained from a patient. The anti-PECAM-1 antibodies can be used to measure the corresponding protein levels by various methods, including but not limited to: (1) standardized ELISA on cell extracts, (2) immunoprecipitation of cell extracts followed by polyacrylamide gel electrophoresis of the immunoprecipitated products and quantitative detection of the band(s) corresponding to PECAM-1, and (3) in situ detection by immunohistochemical straining with the anti-PECAM-1 antibodies and detection with a labeled second antibody. The measurement of the ratio of PECAM-1 to control housekeeping proteins in a cell or cell population is informative regarding the invasive and metastatic status of the cell or cell population.

An antiserum which can be utilized for this purpose can be obtained by conventional procedures. One exemplary procedure involves the immunization of a mammal, such as rabbits, which induces the formation of polyclonal antibodies against PECAM-1. Monoclonal antibodies are also being generated from already immunized hamsters. This antibody can be used to detect the presence and level of the PECAM-1 protein.

It is also possible to use the proteins for the immunological detection of PECAM-1 and associations thereof with standard assays as well as assays using markers, which are radio-immunoassays or enzyme immunoassays.

The detection and determination of PECAM-1 has significant diagnostic importance. For example, the detection of a PECAM-1 decline favoring invasiveness and metastasis would be advantageous in cancer therapy and controlling hypertrophies. The detection or determination of proteins favoring metastasis and invasion will be beneficial in detecting and diagnosing cancer, neurodegenerative diseases, and ischemic cell death. Thus these proteins and their antibodies can be employed as a marker to monitor, check or detect the course of disease.

Cross-linked complexes of PECAM-1 with PECAM-1-interacting polypeptides can be used as immunogens, and the resultant antisera preadsorbed with PECAM-1 and PECAM-1-interacting polypeptide such that the remaining antisera comprises antibodies which bind conformational epitopes present on the complexes but not the monomers (e.g., complex-specific epitopes). Complex-specific hybridomas and monoclonal antibodies can be similarly generated. Such antibodies can be used diagnostically to detect and quantitate the presence of specific complexes and correlate this data with disease or cell type, and the like.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al. Science 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol. 227:381 (1991); Marks et al., J. Mol. Biol. 222:581 (1991)]. The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology, 10:779-783 (1992); Lonberg et al., Nature, 368:856-859 (1994); Morrison, Nature, 368:812-13 (1994); Fishwild et al., Nature Biotechnology, 14:845-51 (1996); Neuberger, Nature Biotechnology, 14:826 (1996); Lonberg and Huszar, Intern. Rev. Immunol., 13:65-93 (1995).

Therapeutic formulations of the antibody are prepared for storage by mixing the antibody having the desired degree of purity with optional pharmaceutically acceptable carriers, excipients or stabilizers (Remington's Pharmaceutical Sciences, 16th edition, Osol, A. ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; anti-oxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN.TM., PLURONICS.TM. or polyethylene glycol (PEG).

The anti-PECAM binding species of the present invention can be administered to a cancer patient in conjunction with other chemotherapeutic agents and radiotherapy sensitizers.

The following examples are given to illustrate the invention, but are not to be limiting thereof. All percentages given throughout the specification are based upon weight unless otherwise indicated. All protein molecular weights are based on mean average molecular weights unless otherwise indicated.

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

EXPERIMENTAL EXAMPLES

Materials and Methods;

Female mice 6-8 weeks of age were used for all studies. C57B1/6 and BalbC mice were purchased from Simonson Labs, (Gilroy, Calif.), and the Nu/Nu mice were purchased from Charles River. Tumor cells were inoculated by tail vein injection. For the B16-F10 murine melanoma tumor and Lewis Lung carcinoma highly metastatic (LLC-HM) lung cancer models, each C57B1/6 mouse received 25,000 tumor cells suspended in 200 µl of culture media. For the 4T1 murine breast cancer and CT26 murine colon cancer models, each Balb/C mouse received 50,000 tumor cells tumor cells suspended in 200 µl of culture media. For the Lox cell human melanoma xenograft model, Nu/Nu mice received a total of 2.5 million Lox cells in culture media in two separate tail vein injections. The first injection was administered in the morning and the second injection four hours later. Each injection contained 1.25 million cells in 300 µl of culture media.

For the first set of experiments, groups of eight mice received 25,000 B16-F10 tumor cells by tail vein injection on day 0, and then received 5 doses of 200 µg of either rat anti-mouse anti-PECAM-1 (mAb 390) (provided by Dr. H. Delisser, University of Pennsylvania) or Rat IgG2(a) isotype control antibody (Sigma) by the following schedules. One group of mice received 5 doses of 200 µg of either rat anti-mouse anti-PECAM-1 (mAb 390) or Rat IgG2(a) isotype control antibody starting on day 0 (just after tumor cell injection), and then on days 1, 3, 6 and 8. In addition, one group of mice received 5 doses of 200 µg of either rat anti-mouse anti-PECAM-1 (mAb 390) or Rat IgG2(a) isotype control antibody starting on day 7 after tumor cell injection, and then on days 8, 10, 13 and 15. Mice bearing CT26, 4T1 B16 and Lox cells were sacrificed on days 20, 22, 23, and 28 after tumor cell inoculation, respectively.

In each case, all mice from the respective group were sacrificed when an index animal looked seriously ill or died, and significant numbers of lung tumors were documented following sacrifice and analysis of dissected lungs. Lungs from each mouse were dissected out and then weighed. The lungs then were infused intra-tracheally with 5% buffered formalin for mice bearing B16-F10 melanoma. For all other tumor-bearing mice (the 4T1, CT26, LLC-HM and Lox tumor models), the lungs were then were infused intra-tracheally with the fixative solution containing Indian ink. All lung samples were then fixed in 5% buffered formalin (50% of 10% buffered formalin (Fisher) and 50% PBS). Lung tumors were counted under a dissecting microscope by an observer blinded to which group from which they came. The potential significance of differences between various groups was assessed using an unpaired, two-sided Student's t Test.

Subsequently, the lungs were subjected to the following studies. Mitotic and apoptotic figures were counted on four-micron hematoxylin and eosin stained slides using a conventional light microscope. Actual counts of mitotic and apoptotic figures were made from the ten largest nodules. Apoptotic bodies and mitotic figures were counted according to previously described morphologic criteria (1, 2). The apoptotic and mitotic rate were calculated based on the degree of tumor cellularity, and expressed as the number of apoptotic or mitotic figures per thousand cells. In situ detection of cleaved, apoptotic DNA fragments (TUNEL) was performed using the TdT-FragEL Detection Kit (Oncogene Science) according to the manufacturer's protocol. The frequency of labeled cells was calculated by counting at least 1,000 cells in areas with the highest number of TdT labeled nuclei. Matrigel assay and Boyden chamber analysis were performed as described (3). All analyses of apoptosis, mitosis, angiogenesis and histopathology were performed by an investigator blinded to the identity of the specimens being assessed. Expression of PECAM-1 on the various tumor cell lines assessed was performed by FACS analysis.

REFERENCES

1. Kerr, J. F., Wyllie, A. H., & Currie, A. R. (1972) *Br. J. Cancer* 26, 239-257.
2. van Diest, P. J., Brugal, G., & Baak, J. P. (1998) *J. Clin. Pathol.* 51, 716-724.
3. Desprez, P. Y., Lin, C. Q., Thomasset, N., Sympson, C. J., Bissell, M. J., & Campisi, J. (1998) *Mol. Cell Biol.* 18, 4577-4588.

Results of the Anti-betastatic Tumor Studies:

Binding of anti of anti-PECAM-1 antibody to the various tumor cell lines tested.

Binding of anti-PECAM-1 antibody to murine B16-F10 melanoma cells, murine 4T1 mammary carcinoma cells and murine Lewis Lung carcinoma-highly metastatic (LLC-HM) cells was assessed.

No PECAM-1 expression (no specific binding of anti-PECAM-1 antibody to any of these cell types was detected (data not shown)). Analysis of PECAM-1 expression on murine CT26 colon tumor cells and human LOX melanoma cells is pending.

Figure 1A:
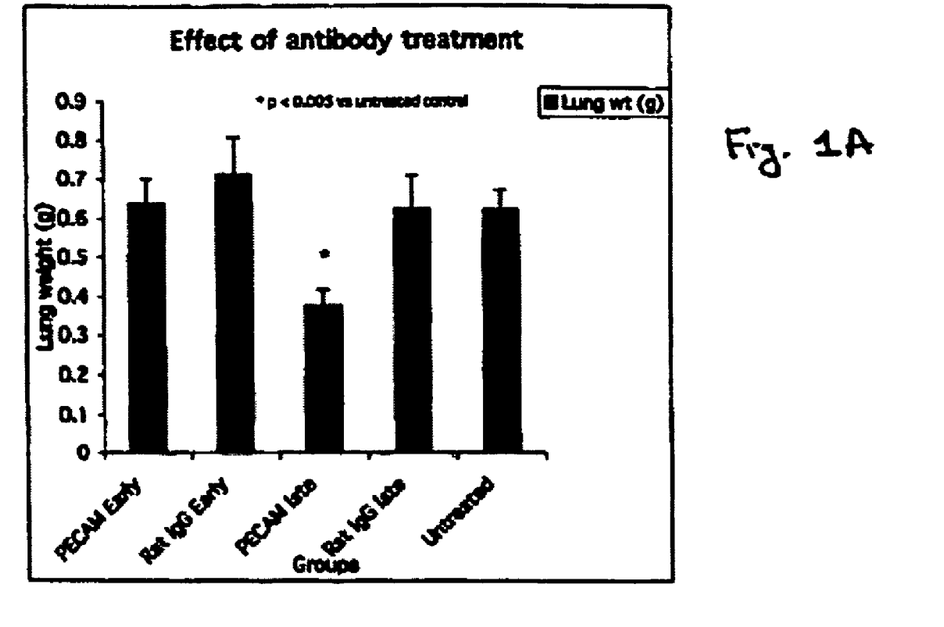
FIGS. 1A and 1B show the effects of antibody treatment in mice.
Figure 1B:
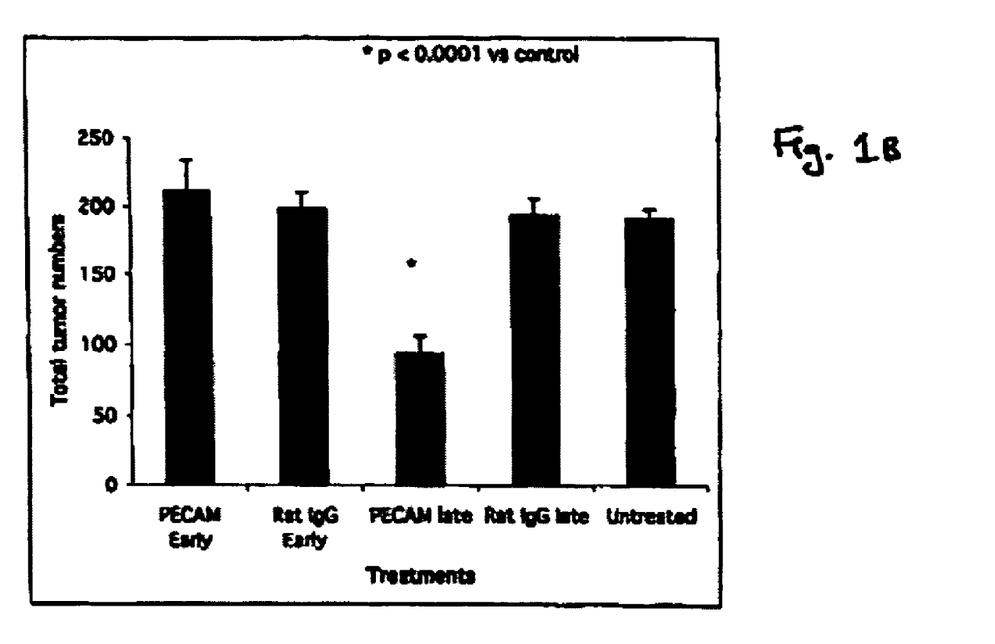

Effects of anti-PECAM-1 on the metastatic progression of B16-F10 melanoma. We first compared the potential anti-tumor effects of five, 200 µg intravenous doses of either anti-PECAM-1 or IgG isotype control antibody, with treatment initiated either on the day of tumor injection (day 0) or 7 days after tumor cell injection (day 7). Injection of IgG isotype control antibody, beginning on either day 0 or day 7, as well as injection of anti-PECAM-1 antibody beginning on day 0 had no effect on either total lung weight (an indicator of overall metastatic burden) or the total number of metastatic lung tumors, when compared to untreated, tumor-bearing control mice. The lack of anti-tumor efficacy produced by anti-PECAM antibody therapy initiated on day 0 contrasts with the results of a prior study testing this dose and schedule of anti-PECAM antibody against locally-inoculated, sub-cutaneous B16 melanoma tumors. In this prior study, five, 200 µg intraperitoneal doses of the same anti-PECAM-1 antibody begun on the same day (day 0) as local sub-cutaneous inoculation of B16 melanoma tumors did produce significant anti-tumor activity, significantly reducing both local tumor growth, as well as significantly reducing tumor angiogenesis (Zhou et al. Angiogenesis 3: 181-188, 1999). In contrast, our studies demonstrated that injection of this same anti-PECAM-1 antibody beginning on day 0 showed no anti-tumor activity against B16 melanoma lung metastases. However, we discovered that intravenous injection of anti-PECAM-1 antibody beginning on day 7 after tumor cell injection was highly effective against metastatic B16 melanoma tumors, significantly reducing both total lung weights (p 0.005) and the total number of metastatic B16-F10 melanoma lung tumors (p<0.0001), when compared to control mice (FIGS. 1A and 1B). Thus, anti-tumor results obtained using IP-administered anti-PECAM antibody against local tumors can differ substantially from those obtained using intravenously-injected anti-PECAM antibody against metastatic tumors.

Figure 2A:
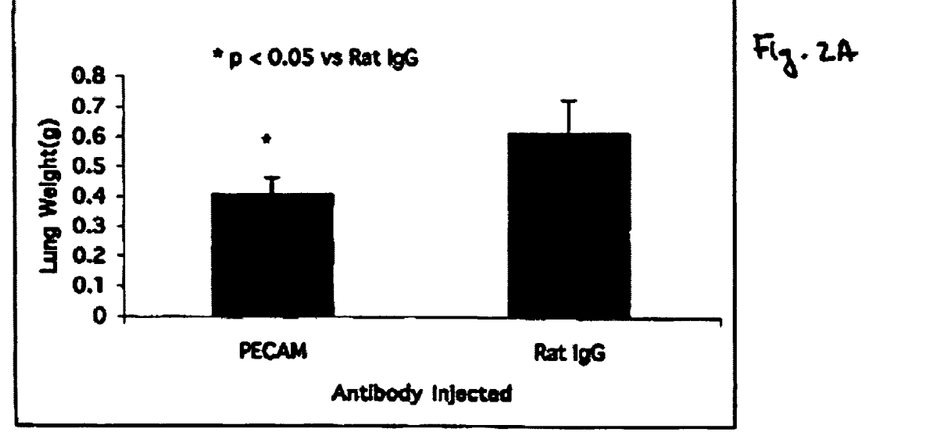
FIGS. 2A and 2B show effects of antibody treatment.
Figure 2B:
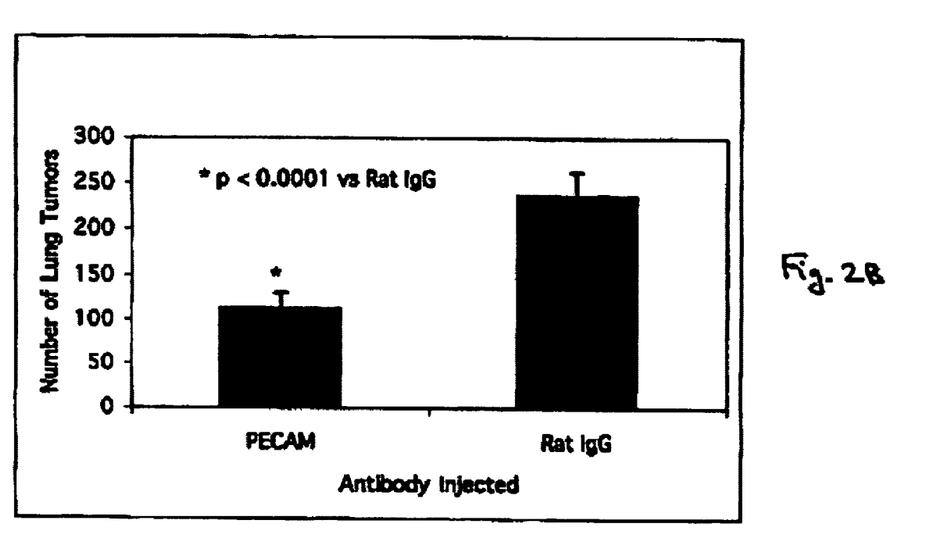

We then attempted to repeat these results in a follow-up experiment, again comparing the effects of either the anti-PECAM-1 antibody or the isotype control, initiated 7 days after IV injection of B16-F10 cells. We found that anti-PECAM-1 antibody significantly reduced both total lung weights (p<0.05) and the total number of lung tumors (p<0.0001) when compared to B16-F10-bearing mice treated with the same schedule and dose of isotype control antibody (FIGS. 2A and 2B). (We used isotype control antibody treated mice as controls in all subsequent experiments because we previously showed that total lung weights and total numbers of lung tumors do not differ between mice treated with isotype control antibody and untreated mice (see FIGS. 1A and 1B)). Anti-PECAM antibody therapy initiated on day 7 after tumor cell injection again significantly reduced overall tumor burden and the total number of lung metastatic tumors, as we had previously observed in experiment 1 above. Intraperitoneal administration of this same anti-PECAM antibody has previously been reported to significantly reduce tumor angiogenesis in subcutaneously inoculated B16 melanoma tumors. We assessed tumor angiogenesis, as well tumor apoptotic and mitotic rates in B16-F10 lung tumors from the anti-PECAM- and isotype control antibody-injected groups. Surprisingly, the number of blood vessels in lung tumors appeared higher in the anti-PECAM-treated group (17.9+4.5 tumor bloodvessels/HPF (avg+S.E.)) than the isotype control-treated group (8.79+2.9), although this difference did not approach statistical significance (p=0.12). The level of tumor apoptosis (9.9+1.1) in anti-PECAM-versus isotype control-treated mice (9.7+0.8) was also comparable. However, the rate of mitosis in tumor cells was significantly higher (p<0.05) in isotype control-treated mice (4.7+0.5) versus anti-PECAM-treated mice (2.9+0.7). Histopathologically, tumor necrosis, hemorrhage, pulmonary congestion and/or intravascular emboli were noted in 7 of 9 isotype control antibody-treated mice, whereas none of these findings were noted in anti-PECAM-1 antibody-treated mice (data not shown). Overall, anti-PECAM antibody therapy significantly reduced the total numbers of metastatic B16-F10 tumors and overall tumor burden, as well as significantly reducing tumor cell mitotic rates and lung histopathologic changes. Anti-PECAM-1 antibody therapy did not reduce either tumor angiogenesis or tumor apoptosis.

To demonstrate that the anti-metastatic activity of anti-PECAM-1 antibody was specific for a broad spectrum of solid tumors, in addition to B16-F10 melanoma tumors, we then tested its potential anti-metastatic activity against a variety of other tumor cell lines injected into mice. These lines included murine 4T1 mammary carcinoma cells, murine CT26 colon tumor cells, murine Lewis Lung carcinoma-highly metastatic (LLC-HM) cells and human LOX melanoma cells. We used established protocols for generating the metastatic spread of each of these lines, as described in the materials and methods section above. We found that five, 200/g doses of IV, anti-PECAM antibody therapy initiated on day 7 produced significant anti-metastatic activity against each of these tumor lines in tumor-bearing mice.

Figure 3A:
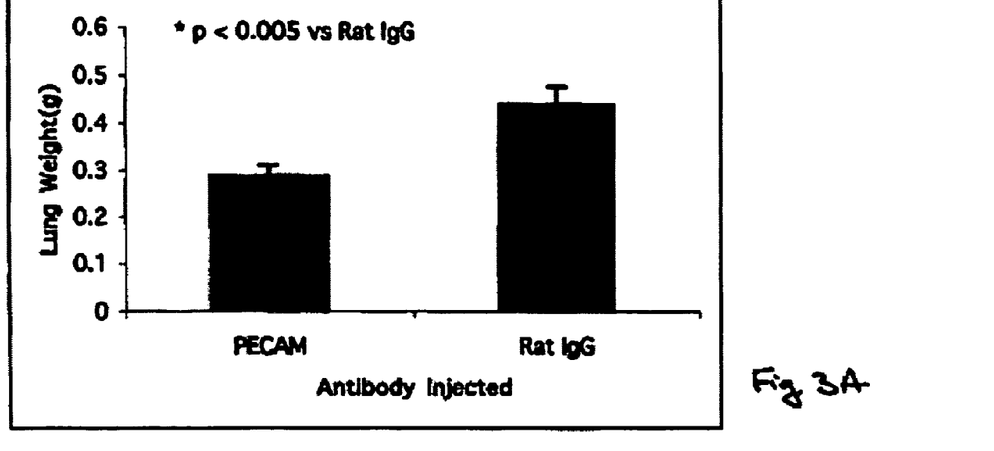
FIGS. 3A and 3B show effects of antibody treatment in mice.
Figure 3B:
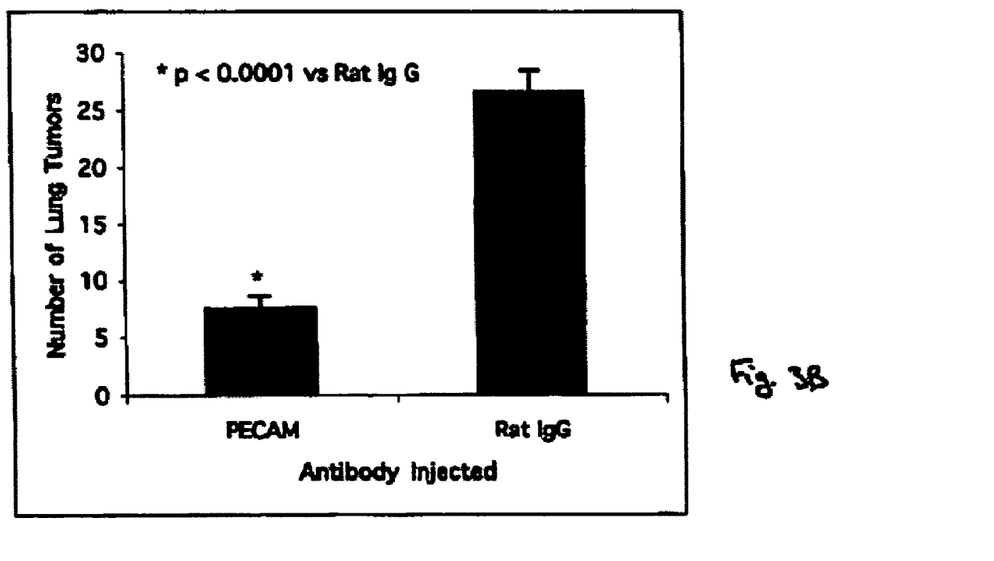

Specifically, anti-PECAM antibody was highly effective against the metastatic spread of 4T1 mammary carcinoma tumors, producing significant reductions of total tumor burden (p<0.005) and total metastatic lung tumors (p<0.0001), when compared to isotype control antibody-treated mice (see FIGS. 3A and 3B). Again contrary to previous reports by others, even though anti-PECAM antibody therapy was highly effective against the metastatic spread of 4T1 tumors, it had no effect on tumor vascularity, since anti-PECAM-treated mice showed 27.8+2.5 tumor blood vessels/HPF, whereas isotype control-treated mice showed 26.5+2.1 tumor blood vessels/HPF (data not shown). Thus, unlike the anti-tumor effects of this same anti-PECAM antibody against sub-cutaneous tumors (Zhou et al. Angiogenesis 3: 181-188, 1999), anti-PECAM antibody effects against metastatic tumors does not appear to be mediated through effects on tumor angiogenesis. (The analysis the effects of anti-PECAM antibody on tumor mitotic and apoptotic rates for 4T1 tumors is in progress).

Figure 4A:
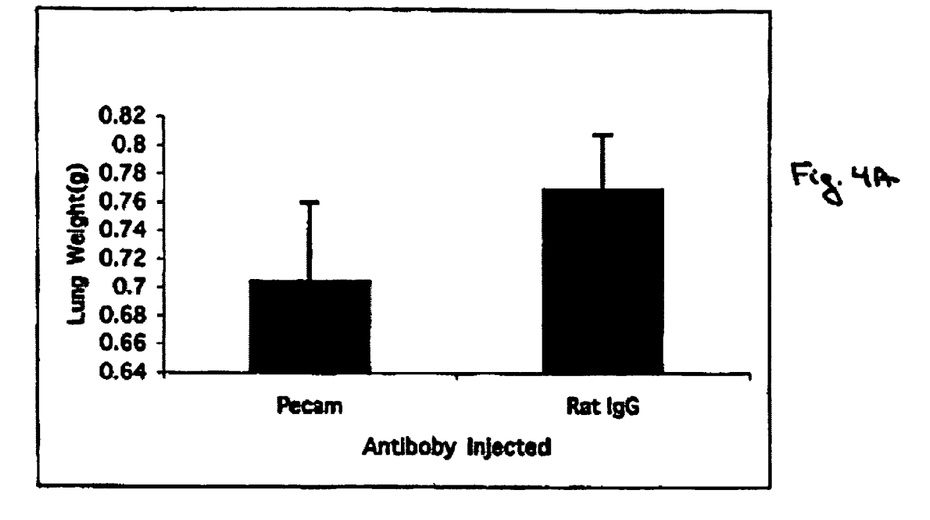
FIGS. 4A and 4B show effects of antibody treatment in mice.
Figure 4B:
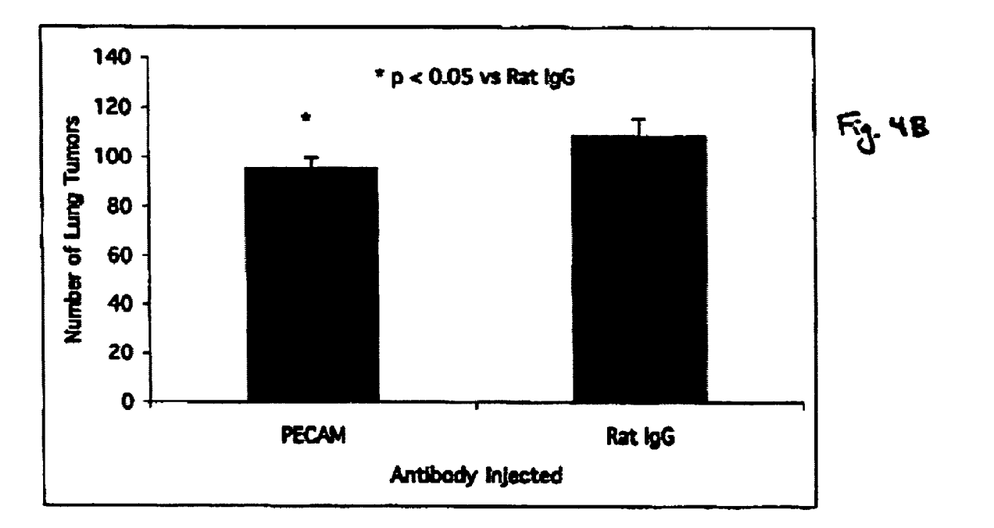

Anti-PECAM antibody was less active against the metastatic spread of CT26 colon tumors, but still significantly reduced the total number of metastatic lung tumors (p<0.05), when compared to isotype control antibody-treated mice (see FIGS. 4A and 4B).

Anti-PECAM antibody therapy did not significantly reduce (p=0.74) lung weights in mice bearing LLC-HM tumors (0.85±0.2 gm) when compared to isotype control antibody-treated mice (0.94±0.1 gm). Since lung metastases grew largely as confluent masses rather than discrete tumors in this experiment, it was not possible to accurately count the numbers of individual lung tumors in mice. However, the number of extrapulmonary lung metastases appeared to be significantly reduced in the anti-PECAM antibody treated mice. Specifically, all eight of eight isotype control-treated mice showed discrete, bulky extrapulmonary tumors in the thoracic cavity, whereas of only 3 of 9 anti-PECAM antibody treated mice showed extrapulmonary tumors. (Note, one of the nine isotype control antibody-treated mice died with an extensive tumor burden 4 days before all other mice were sacrificed. This mouse was not included in the final analysis of metastatic LLC-HM tumors. In addition, 3 of 8 isotype control-treated mice showed liver metastases, whereas of only 1 of 9 anti-PECAM antibody treated mice showed liver tumors. Thus, while not clearly reducing the number of lung metastatic LLC-HM tumors, anti-PECAM antibody therapy did appear to significantly reduce the extrapulmonary spread of LLC-HM tumors.

Figure 5A:
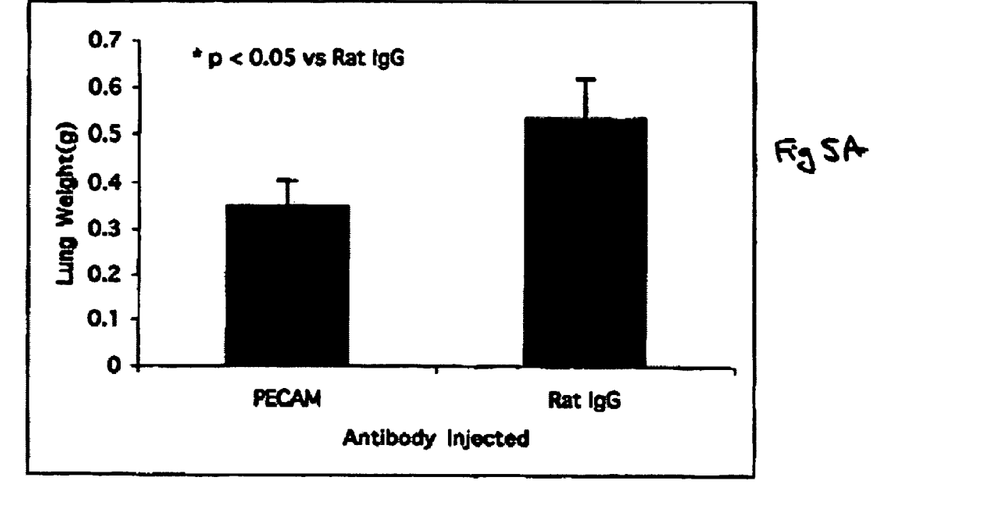
FIGS. 5A and 5B show effects of antibody treatment.
Figure 5B:
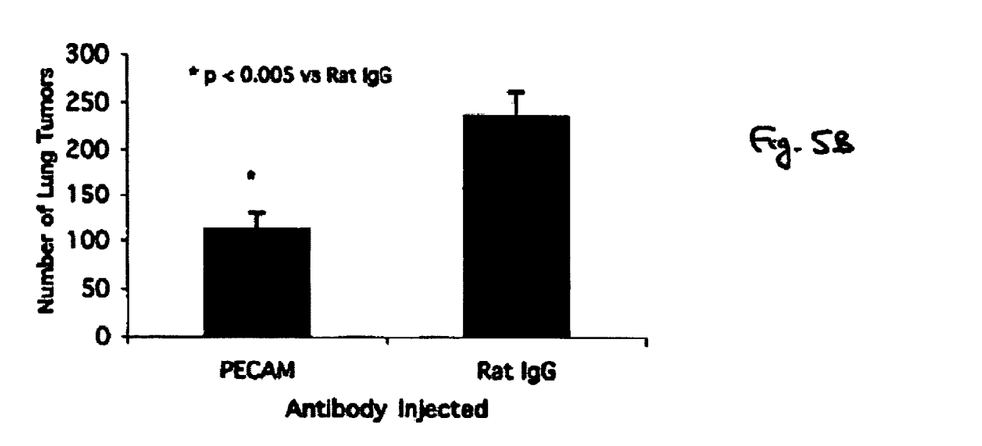

Last, since anti-PECAM antibody therapy reduced the metastatic spread of four different murine solid tumors in immunocompetent, syngeneic mouse strains, we assessed whether anti-PECAM antibody therapy altered the metastatic spread of human LOX xenograft tumors in nude mice. As in the murine tumor models, anti-PECAM antibody therapy significantly reduced the metastatic spread of LOX cells in nude mice, as measured by both lungs weights (p<0.05) and the total number of lung tumors (p<0.005) when compared to LOX-bearing mice treated with isotype control antibody (see FIGS. 5A and 5B).

Taken together, these data show that systemic, anti-PECAM antibody therapy can significantly reduce the metastatic spread of a wide variety of common fatal solid tumors (melanoma, breast, colon and lung cancer) in mouse metastasis models. Importantly, none of the tumor cells tested express detectable PECAM-1, indicating that anti-PECAM antibody does not produce its anti-metastatic tumor effects via direct binding to the tumor cells themselves. Rather, anti-PECAM antibody appears to function as an anti-tumor agent via binding to PECAM-1 expressed on vascular endothelial cells. However, anti-PECAM antibody does not appear exert anti-metastatic activity by effects on tumor blood vessel formation. Thus, unlike anti-tumor antibodies currently used to treat human cancers, anti-PECAM is neither tumor type specific, nor does it require expression of its cognate receptor on tumor cells to produce significant anti-metastatic effects.

The invention claimed is:

1. A method for repressing metastasis of a neoplastic cell, the method comprising administering a therapeutically effective amount of an anti-PECAM antibody via systemic administration to a mammal having one or more metastases.

2. The method of claim 1, wherein the anti-PECAM antibody is a monoclonal antibody.

3. The method of claim 1, wherein the neoplastic cell is a melanoma cell, a breast carcinoma cell, colon carcinoma cell, or a lung carcinoma cell.

4. The method of claim 1, wherein the neoplastic cell is a human cell.

5. The method of claim 2, wherein the monoclonal antibody is administered to the mammal via intraperitoneal injection.

6. The method of claim 2, wherein the administration of monoclonal antibody is commenced after tumor growth has been established in said mammal.

7. The method of claim 6, wherein the monoclonal antibody is administered after tumor cells have been present in the circulatory system of said mammal for at least 7 days prior to said administration of monoclonal antibody.

8. The method of claim 6, wherein the neoplastic cells are human tumor cells.

9. The method of claim 1, wherein the anti-PECAM antibody is administered to the mammal in a plurality of doses wherein each dose comprises at least 200 micrograms of anti-PECAM antibody and said plurality of doses comprise at least five doses with each dose administered at least two days apart.

10. The method of claim 9, wherein the antibody is administered after tumor cells have been present in the circulatory system of said mammal for at least 7 days prior to said administration of antibody.

11. The method of claim 1, wherein the antibody is administered to the mammal via intravenous injection.

* * * * *